(12) United States Patent
Sailland et al.

(10) Patent No.: US 6,268,549 B1
(45) Date of Patent: Jul. 31, 2001

(54) DNA SEQUENCE OF A GENE OF HYDROXY-PHENYL PYRUVATE DIOXYGENASE AND PRODUCTION OF PLANTS CONTAINING A GENE OF HYDROXY-PHENYL PYRUVATE DIOXYGENASE AND WHICH ARE TOLERANT TO CERTAIN HERBICIDES

(75) Inventors: Alain Sailland; Anne Rolland; Michel Matringe, all of Lyons (FR); Ken Pallett, Ongar Essex (GB)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 08/945,515

(22) PCT Filed: Jun. 3, 1996

(86) PCT No.: PCT/FR96/00831

§ 371 Date: Feb. 18, 1998

§ 102(e) Date: Feb. 18, 1998

(87) PCT Pub. No.: WO96/38567

PCT Pub. Date: Dec. 5, 1996

(30) Foreign Application Priority Data

| | | | |
|---|---|---|---|
| Jun. 2, 1995 | (FR) | ................ | 95/06800 |
| Nov. 10, 1995 | (FR) | ................ | 95/13570 |
| May 17, 1996 | (FR) | ................ | 96/05944 |

(51) Int. Cl.⁷ .............................. A01H 5/00; A01H 1/02; C07H 21/04

(52) U.S. Cl. ................ 800/295; 800/298; 800/278; 800/275; 536/23.5; 536/23.6; 536/23.7; 536/24.1; 435/468; 435/419

(58) Field of Search .................... 800/295, 298, 800/278, 275; 536/23.5, 23.6, 23.7, 24.1; 435/468, 419, 320.1

(56) References Cited

U.S. PATENT DOCUMENTS 5,635,618   6/1997   Capellades .

FOREIGN PATENT DOCUMENTS

| | | |
|---|---|---|
| 0507698 A1 | 10/1992 | (EP) . |
| 0508909 A1 | 10/1992 | (EP) . |
| 0614970 A2 | 2/1994 | (EP) . |
| 0652286 A1 | 5/1995 | (EP) . |
| WO 97/27285 | 7/1997 | (WO) . |

OTHER PUBLICATIONS

Napoli et al. The Plant Cell. vol. 2, 279–289, 1992.*
Endo et al. The Journal of Biological Chemistry vol. 267, No. 34, pp. 24235–24240, Dec. 1992.*
Denoya et al. Journal of Bacteriology, pp. 5312–5319, Sep. 1994.*
Awata et al. Genomics 23, 534–539, 1994 Oct. 1994.*
Norris et al., The Plant Cell, 7:2129 (1995).
Newman et al., Plant Phy. 106:1241 (1994).
Ruetschi et al., Euro. J. Biochem. 205:459 (1992).
Secor, Plant Phys.. 106:1429 (1994).
Schultz et al., FEBS 318:162 (1993).
Prisbylla et al., Brighton Crop Protection Conference (1993).
Norris et al., Am. Soc. Plant Phys., Meeting Abstract (1996).
Endo et al., J. Biol. Chem. 267:24235 (1992).
Wintermeyer et al., Inf. & Imm. 62:1109 (1994).
Awata et al., Genomics 23:534 (1994).
Ruzafa et al., FEMS Microbiology Letters 124:179 (1994).
Misawa et al., The Plant Journal 6:481 (1994).
Barta et al., Pesticide Science 45:286 (1995).
Gugi et al., J. Bacteriology 173:3814 (1991).
Fuqua et al., Gene 109:131 (1991).
Denoya et al., J. Bacteriology 176:5312 (1994).
Wyckoff et al., Gene 161:107 (1995).
Lenne et al., from "Photosynthesis:from Light to the Biosphere", pp. 285–288 (1995).
Newman, Sequence AT 952, Accession T 20952.
Newman, Sequence AT 76417, Accession N65764.
Pub. Med. Protein Query results (24 pages total).

* cited by examiner

*Primary Examiner*—Gary Benzion
(74) *Attorney, Agent, or Firm*—Connolly Bove Lodge & Hutz LLP

(57) ABSTRACT

An isolated gene from Pseudomonas is described which expresses a hydoxy phenyl pyruvate dioxygenase. Also described are chimeric genes for introduction into plants to overexpress a hydoxy phenyl pyruvate dioxygenase and produce plants which are tolerant to herbicides.

15 Claims, 3 Drawing Sheets

```
GCNGAYYTNTAYGARAAYCCNATGG GNYTNATGGGNTTYGARTTYATHGA RYTNGCNWSNCCNACNCCNAAYACN      75
A  D  L  Y  E  N  P  M  G  L  M  G  F  E  F  I  E  L  A  S  P  T  P  N  T
              ──────────────▶

YTNGARCCNATHTTYGARATHATGG GNTTYACNAARGTNGCNACNCAYMG NWSNAARGAYGTNCAYYTNTAYMGN     150
L  E  P  I  F  E  I  M  G  F  T  K  V  A  T  H  R  S  K  D  V  H  L  Y  R

CARGGNGCNATHAAYYTNATHYTNA AYAAYGARCCNCAYWSNGTNGCNWS NTAYTTYGCNGCNGARCAYGGNCCN     225
Q  G  A  I  N  L  I  L  N  N  E  P  H  S  V  A  S  Y  F  A  A  E  H  G  P

WSNGTNTGYGGNATGGCNTTYMGNG TNAARGAYWSNCARAARGCNTAYAA RMGNGCNYTNGARYTNGGNGCNCAR     300
S  V  C  G  M  A  F  R  V  K  D  S  Q  K  A  Y  K  R  A  L  E  L  G  A  Q

CCNATHCAYATHGARACNGGNCCNA TGGARYTNAAYYTNCCNGCNATHAA RGGNATHGGNGGNGCNCCNYTNTAY     375
P  I  H  I  E  T  G  P  M  E  L  N  L  P  A  I  K  G  I  G  G  A  P  L  Y
              ──────────────▶

YTNATHGAYMGNTTYGGNGARGGNW SNWSNATHTAYGAYATHGAYTTYGT NTTYYTNGARGGNGTNGAYMGNCAY     450
K  I  D  R  F  G  E  G  S  S  I  Y  D  I  D  F  V  F  L  E  G  V  D  R  H

CCNGTNGGNGCNGGNYTNAARATHA THGAYCAYYTNACNCAYAAYGTNTA YMGNGGNMGNATGGCNTAYTGGGCN     525
P  V  G  A  G  L  K  I  I  D  H  L  T  H  N  V  Y  R  G  R  M  A  Y  W  A

AAYTTYTAYGARAARYTNTTYAAYT TYMGNGARATHMGNTAYTTYGAYAT HAARGGNGARTAYACNGGNYTNACN     600
N  F  Y  E  K  L  F  N  F  R  E  I  R  Y  F  D  I  K  G  E  Y  T  G  L  T

WSNAARGCNATGACNGCNCCNGAYG GNATGATHMGNATHCCNYTNAAYGA RGARWSNWSNAARGGNGCNGGNCAR     675
S  K  A  M  T  A  P  D  G  M  I  R  I  P  L  N  E  E  S  S  K  G  A  G  Q

ATHGARGARTTYYTNATGCARTTYA AYGGNGARGGNATHCARCAYGTNGC NTTYYTNWSNGAYGAYYTNATHAAR     750
I  E  E  F  L  M  Q  F  N  G  E  G  I  Q  H  V  A  F  L  S  D  D  L  I  K
              ◀──────────────              ◀──────────────

ACNTGGGAYCAYYTNAARWSNATHG GNATGMGNTTYATGACNGCNCCNCC NGAYACNTAYTAYGARATGYTNGAR     825
T  W  D  H  L  K  S  I  G  M  R  F  M  T  A  P  P  D  T  Y  Y  E  M  L  E

GGNMGNYTNCCNAAYCAYGGNGARC CNGTNGGNGARYTNCARGCNMGNGG NATHYTNYTNGAYGGNWSNWSNGAR     900
G  R  L  P  N  H  G  E  P  V  G  E  L  Q  A  R  G  I  L  L  D  G  S  S  E

WSNGGNGAYAARMGNYTNYTNYTNC ARATHTTYWSNGARACNYTNATGGG NCCNGTNTTYTTYGARTTYATHCAR     975
S  G  D  K  R  L  L  L  Q  I  F  S  E  T  L  M  G  P  V  F  F  E  F  I  Q

MGNAARGGNGAYGAYGGNTTYGGNG ARGGNAAYTTYAARGCNYTNTTYGA RWSNATHGARMGNGAYCARGTNMGN    1050
R  K  G  D  D  G  F  G  E  G  N  F  K  A  L  F  E  S  I  E  R  D  Q  V  R
                            ◀──────────────

MGNGGNGTNYTNWSNACNGAY                                                          1071
R  G  V  L  S  T  D
```

FIG. 1

```
Consensus         .ADLYENPMG LMGFEFIE.A SPTP.TLEPI FEIMGFTKVA THRSK.VHLY    50
P. fluorescens    M.........  ........F.  .....G....  ..........  .....N....    50
Pseudomonas sp.   -.........  ........L.  .....N....  ..........  .....D....    49

Consensus         RQG.INLILN NEP.S.ASYF AAEHGPSVCG MAFRVKDSQK AY.RALELGA   100
P. fluorescens    ...E......  ...N.I....  ..........  .....N....  ..........   100
Pseudomonas sp.   ...A......  ...H.V....  ..........  .....K....  ..........    99

Consensus         QPIHI.TGPM ELNLPAIKGI GGAPLYLIDR FGEGSSIYDI DFV.LEGV.R   150
P. fluorescens    .....D....  ..........  ..........  ..........  ...Y..E...   150
Pseudomonas sp.   .....E....  ..........  ..........  ..........  ...F..D...   149

Consensus         .PVGAGLK.I DHLTHNVYRG RM.YWANFYE KLFNFRE.RY FDIKGEYTGL   200
P. fluorescens    N....V....  ..........  ..V.......  .......A..  ..........   200
Pseudomonas sp.   H......I..  ..........  ..A.......  .......I..  ..........   199

Consensus         TSKAM.APDG MIRIPLNEES SKGAGQIEEF LMQFNGEGIQ HVAFL.DDL.   250
P. fluorescens    .....S....  ..........  ..........  ..........  .....T...V   250
Pseudomonas sp.   .....T....  ..........  ..........  ..........  .....S...I   249

Consensus         KTWD.LK.IG MRFMTAPPDT YYEMLEGRLP .HGEPV..LQ ARGILLDGSS   300
P. fluorescens    ....A..K..  ..........  ..........  D.....DQ..  ..........   300
Pseudomonas sp.   ....H..S..  ..........  ..........  N.....GE..  ..........   299

Consensus         ..GDKRLLLQ IFSETLMGPV FFEFIQRKGD DGFGEGNFKA LFESIERDQV   350
P. fluorescens    VE........  ..........  ..........  ..........  ..........   350
Pseudomonas sp.   ES........  ..........  ..........  ..........  ..........   349

Consensus         RRGVL..D                                                  358
P. fluorescens    .....TA.                                                  358
Pseudomonas sp.   .....ST.                                                  357
```

FIG. 3

SEQUENCE LISTING

<160> NUMBER OF SEQ ID NOS: 3

<210> SEQ ID NO 1
<211> LENGTH: 1077
<212> TYPE: DNA
<213> ORGANISM: Pseudomonas

<400> SEQUENCE: 1

| | | | | | |
|---|---|---|---|---|---|
| atggcagatc | tatacgaaaa | cccaatgggc | ctgatgggct | ttgaattcat | cgaattcgcg | 60 |
| tcgccgacgc | cgggtaccct | ggagccgatc | ttcgagatca | tgggcttcac | caaagtcgcg | 120 |
| acccaccgtt | ccaagaacgt | gcacctgtac | cgccagggcg | agatcaacct | gatcctcaac | 180 |
| aacgagccca | cagcatcgc | ctcctacttt | gcggccgaac | acggcccgtc | ggtgtgcggc | 240 |
| atggcgttcc | gcgtgaagga | ctcgcaaaag | gcctacaacc | gcgccctgga | actcggcgcc | 300 |
| cagccgatcc | atattgacac | cgggccgatg | gaattgaacc | tgccggcgat | caagggcatc | 360 |
| ggcggcgcgc | cgttgtacct | gatcgaccgt | tcggcgaag | gcagctcgat | ctacgacatc | 420 |
| gacttcgtgt | acctcgaagg | tgtggagcgc | aatccggtcg | gtgcaggtct | caaagtcatc | 480 |
| gaccacctga | cccacaacgt | ctatcgcggc | cgcatggtct | actgggccaa | cttctacgag | 540 |
| aaattgttca | acttccgtga | agcgcgttac | ttcgatatca | agggcgagta | caccggcctg | 600 |
| acttccaagg | ccatgagtgc | gccggacggc | atgatccgca | tcccgctgaa | cgaagagtcg | 660 |
| tccaagggcg | cggggcagat | cgaagagttc | ctgatgcagt | tcaacggcga | aggcatccag | 720 |
| cacgtggcgt | tcctcaccga | cgacctggtc | aagacctggg | acgcgttgaa | gaaaatcggc | 780 |
| atgcgcttca | tgaccgcgcc | gccagacact | tattacgaaa | tgctcgaagg | ccgcctgcct | 840 |
| gaccacggcg | agccggtgga | tcaactgcag | gcacgcggta | tcctgctgga | cggatcttcc | 900 |
| gtggaaggcg | acaaacgcct | gctgctgcag | atcttctcgg | aaaccctgat | gggcccggtg | 960 |
| ttcttcgaat | tcatccagcg | caagggcgac | gatgggtttg | gcgagggcaa | cttcaaggcg | 1020 |
| ctgttcgagt | ccatcgaacg | tgaccaggtg | cgtcgtggtg | tattgaccgc | cgattaa | 1077 |

<210> SEQ ID NO 2
<211> LENGTH: 1338
<212> TYPE: DNA
<213> ORGANISM: Arabidopsis

<400> SEQUENCE: 2

| | | | | | |
|---|---|---|---|---|---|
| atgggccacc | aaaacgccgc | cgtttcagag | aatcaaaacc | atgatgacgg | cgctgcgtcg | 60 |
| tcgccgggat | tcaagctcgt | cggatttccc | aagttcgtaa | gaaagaatcc | aaagtctgat | 120 |
| aaattcaagg | ttaagcgctt | ccatcacatc | gagttctggt | gcggcgacgc | aaccaacgtc | 180 |
| gctcgtcgct | tctcctgggg | tctggggatg | agattctccg | ccaaatccga | tctttccacc | 240 |
| ggaaacatgg | ttcacgcctc | ttacctactc | acctccggtg | acctccgatt | ccttttcact | 300 |
| gctccttact | ctccgtctct | ctccgccgga | gagattaaac | cgacaaccac | agcttctatc | 360 |
| ccaagtttcg | atcacggctc | ttgtcgttcc | ttcttctctt | cacatggtct | cggtgttaga | 420 |
| gccgttgcga | ttgaagtaga | agacgcagag | tcagctttct | ccatcagtgt | agctaatggc | 480 |
| gctattcctt | cgtcgcctcc | tatcgtcctc | aatgaagcag | ttacgatcgc | tgaggttaaa | 540 |
| ctatacggcg | atgttgttct | ccgatatgtt | agttacaaag | cagaagatac | cgaaaaatcc | 600 |
| gaattcttgc | agggttcga | gcgtgtagag | gatgcgtcgt | cgttcccatt | ggattatggt | 660 |
| atccggcggc | ttgaccacgc | cgtgggaaac | gttcctgagc | ttggtccggc | tttaacttat | 720 |

-continued

```
gtagcggggt tcactggttt tcaccaattc gcagagttca cagcagacga cgttggaacc      780
gccgagagcg gtttaaattc agcggtcctg gctagcaatg atgaaatggt tcttctaccg      840
attaacgagc cagtgcacgg aacaaagagg aagagtcaga ttcagacgta tttggaacat      900
aacgaaggcg cagggctaca acatctggct ctgatgagtg aagacatatt caggaccctg      960
agagagatga ggaagaggag cagtattgga ggattcgact tcatgccttc tcctccgcct     1020
acttactacc agaatctcaa gaacgggtc ggcgacgtgc tcagcgatga tcagatcaag      1080
gagtgtgagg aattagggat tcttgtagac agagatgatc aagggacgtt gcttcaaatc     1140
ttcacaaaac cactaggtga caggccgacg atatttatag agataatcca gagagtagga    1200
tgcatgatga agatgagga agggaaggct taccagagtg gaggatgtgg tggttttggc      1260
aaaggcaatt tctctgagct cttcaagtcc attgaagaat acgaaaagac tcttgaagcc    1320
aaacagttag tgggatga                                                 1338
```

<210> SEQ ID NO 3
<211> LENGTH: 1329
<212> TYPE: DNA
<213> ORGANISM: Daucas Carota

<400> SEQUENCE: 3

```
atggggaaaa acaatcgga agctgaaatt ctctcaagca attcatcaaa cacctctcct       60
gcaacattca agctggtcgg tttcaacaac ttcgtccgcg ccaaccccaa gtccgatcac      120
ttcgccgtga agcggttcca ccacattgag ttctggtgcg gcgacgccac caacacgtcg      180
cggcggttct cgtggggcct cggcatgcct ttggtggcga atcggatct ctctactggc       240 aactctgttc acgcttctta tcttgttcgc tcggcgaatc tcagtttcgt cttcaccgct      300
ccttactctc cgtccacgac cacttcctct ggttcagctg ccatcccgtc tttctcggcc     360
tcgggttttc actcttttgc ggccaagcac ggccttgctg ttcgggctat gctcttgaa      420 gttgctgacg tggctgctgc gtttgaggcc agtgttgcgc gtggggccag gccggcgtcg     480
gctcctgttg aactgggcga ccaggcgtgg ttggcggagg tggagttgta cggagatgtg     540
gtcttgaggt ttgttagttt tgggagggag gagggtttgt ttttgcctgg attcgaggcg     600
gtggagggga tggcgtcgtt tccggatttg gattatgaa ttagaagact tgatcatgcg      660
gtggggaatg ttaccgagtt ggggcctgtg gtggagtata ttaaagggtt tacgggggttt   720 catgaatttg cggagtttac agcggaggat gtggggactt ggagagtgg gttgaattcg      780 gtggtgttgg cgaataacga ggagatggtt ctgttgccct gaatgagcc tgtgtatggg      840 accaagagga agagtcagat acagacttac ttggagcaca atgaagggc tggagtgcag      900 catttggctt tagtgagtga ggatattttt aggactttga gggagatgag gaagaggagt     960
tgcctcggtg gttttgagtt tatgccttcg ccaccgccta cgtattacaa gaatttgaag    1020 aataggtgtcg gggatgtgtt gagtgatgaa cagatcaagg agtgtgaaga tttggggatt  1080
ttggtggata gggatgatca gggtacattg cttcaaatct ttaccaagcc tgtaggtgac   1140
aggcctacct tattcataga gatcattcag agggtagggt gcatgctcaa ggatgatgca  1200
gggcagatgt accagaaggg cgggtgcgga ggatttggga aggggaactt ctcagagctg   1260
ttcaagtcca tcgaagaata tgaaaaaaca cttgaagcta aacaaatcac tggatctgct  1320
gctgcatga                                                          1329
```

DNA SEQUENCE OF A GENE OF HYDROXY-PHENYL PYRUVATE DIOXYGENASE AND PRODUCTION OF PLANTS CONTAINING A GENE OF HYDROXY-PHENYL PYRUVATE DIOXYGENASE AND WHICH ARE TOLERANT TO CERTAIN HERBICIDES

The present invention relates to a hydroxyphenylpyruvate dioxygenase (HPPD) gene, a chimeric gene comprising this gene as coding sequence and its use to obtain plants resistant to certain herbicides.

Certain herbicides have been disclosed, such as the isoxazoles described especially in the French Patent Applications 95 06800 and 95 13570 and especially isoxaflutole, a selective maize herbicide, diketonitriles such as those described in European Applications 0 496 630, 0 496 631, in particular 2-cyano-3-cyclopropyl-1- (2-$SO_2CH_3$-4-$CF_3$-phenyl)propane-1,3-dione and 2-cyano-3-cyclopropyl-1-(2-$SO_2CH_3$-4-2,3-$Cl_2$-phenyl)propane-1,3-dione, triketones described in European Applications 0 625 505 and 0 625 508, in particular sulcotrione. However, a tolerance gene to such herbicides has not been described.

Hydroxyphenylpyruvate dioxygenase is an enzyme which catalyses the conversion reaction of para-hydroxyphenylpyruvate into homogentisate.

In addition, the amino-acid sequence of hydroxyphenylpyruvate dioxygenase from Pseudomonas sp. P.J. 874 has been described, without there being a description of its role in the tolerance of the plants to herbicides (Rüetschi et al.: Eur. J. Biochem. 205, 459–466, 1992). This document does not give a description of the gene coding for this protein.

There have now been discovered the sequence of a gene of this type and that such a gene can, once incorporated into plant cells, produce an over-expression or an activation of HPPD in the plants giving to the latter an worthwhile tolerance to certain novel herbicides, such as those of the isoxazoles family or that of the triketones.

An object of the present invention is an isolated DNA sequence of a gene of non-human origin of a non-marine bacterium, or alternatively of a plant gene, or a sequence which can hybridize with this sequence, characterized in that it expresses a hydroxyphenylpyruvate dioxygenase (HPPD).

More particularly, this sequence can be of bacterial origin, such as especially the genus Pseudomonas or alternatively of plant origin, such as especially of monocotyledonous or dicotyledonous plants, especially of Arabidopsis or of Umbelliferae, such as, for example, the carrot (*Daucus carotta*). It can be native or wild or possibly mutated while at the same time fundamentally retaining a property of herbicidal tolerance against HPPD inhibitors, such as herbicides of the isoxazoles family or that of the triketones.

The invention likewise relates to a process of isolating the above gene, characterized in that:
as primers, some oligonucleotides from the amino-acid sequence of an HPPD are chosen,
starting from these primers, amplification fragments are synthesized by PCR
the gene is isolated by creation and screening of a genomic bank and
the gene is cloned.

Preferably, primers from the HPPD sequence of a bacterium of the genus Pseudomonas is used. Particularly preferably, they are from *Poeudomonas fluorescens*.

The invention also relates to the use of a gene coding for HPPD in a process for the transformation of plants, as a marker gene or as a coding sequence allowing tolerance to certain herbicides to be conferred on the plant. It can likewise be used, in association with other marker genes and/or coding sequences, for an agronomic property.

The coding gene can be of any origin, native or wild or possibly mutated, while at the same time fundamentally retaining a property of herbicidal tolerance against inhibitors of HPPD, such as herbicides of the isoxazoles family or that of the triketones. As coding sequence, especially that described above can be used.

The transformation of plant cells can be achieved by any appropriate known means. A series of methods consists in bombarding cells or protoplasts with particles to which are coupled the DNA sequences.

Another series of methods consists in using, as means of transfer into the plant, a chimeric gene inserted into a Ti plasmid of *Agrobacterium tumefaciens* or Ri plasmid of *Agrobacterium rhizogenes*.

An object of the present invention is also a chimeric gene comprising, in the transcription direction, at least one promoter regulation sequence, a heterologous coding sequence which expresses hydroxyphenylpyruvate dioxygenase and at least one terminator or polyadenylation regulation sequence.

The promoter regulation sequence used can be any promoter sequence of a gene which is naturally expressed in plants, in particular a promoter of bacterial, viral or plant origin, such as, for example, that of a gene of the small subunit of ribulose biscarboxylase (RuBisCo) or that of a gene of α-tubulin (European Application EP No. 0 652 286), or alternatively of a plant virus gene such as, for example, that of cauliflower mosaic virus (CAMV 19S or 35S), but any suitable promoter can be used. Preferably, recourse is made to a promoter regulation sequence which favours the overexpression of the coding sequence, such as, for example, that comprising at least one histone promoter such as described in European Application EP 0507698.

According to the invention, it is equally possible to use, in association with the promoter regulation sequence, other regulation sequences which are situated between the promoter and the coding sequence, such as "enhancer" transcription activators, such as, for example, tobacco etch virus (TEV) translation activator described in the Application WO87/07644, or of transit peptides, either single, or double, and in this case possibly separated by an intermediate sequence, that is to say comprising, in the transcription direction, a sequence coding for a transit peptide of a plant gene coding for a plastid localization enzyme, a part of the sequence of the N-terminal mature part of a plant gene coding for a plastid localization enzyme, then a sequence coding for a second transit peptide of a plant gene coding for a plastid localization enzyme, formed by a part of the sequence of the N-terminal mature part of a plant gene coding for a plastid localization enzyme, such as described in European Application No. 0 508 909.

It is possible to use as terminator or polyadenylation regulation sequence any corresponding sequence of bacterial origin, such as, for example, the nos terminator of *Agrobacterium tumefaciens,* or even of plant origin, such as, for example, a histone terminator such as described in European Application EP No. 0 633 317.

An object of the present invention is also plant cells, of monocotyledonous or dicotyledonous plants, especially of crops, transformed according to one of the processes described above and comprising in their genome an efficacious quantity of a, gene expressing hydroxyphenylpyruvate dioxygenase (HPPD). It has been observed that transformed plants of this type have a significant tolerance to certain novel herbicides such as the isoxazoles described especially in French Patent Applications 9506800 and 95 13570 and especially of 4-[4-CF$_3$-2-(methylsulphonyl)benzoyl]-5-cyclopropylisoxazole, and especially isoxaflutole, a selective maize herbicide, the diketonitriles such as those described in European Applications 0 496 630, 0 496 631, in particular 2-cyano-3-cyclopropyl-1-(2-SO$_2$CH$_3$-4-CF$_3$-phenyl)propane-1,3-dione and 2-cyano-3-cyclopropyl-1-(2-SO$_2$CH$_3$-4-2,3-Cl$_2$-phenyl)propane-1,3-dione, the triketones described in European Applications 0 625 505 and 0 625 508, in particular sulcotrione.

Finally, an object of the invention is a method of weeding plants, especially crops, with the aid of a herbicide of this type, characterized in that this herbicide is applied to plants transformed according to the invention, both pre-sowing, pre-emergence and post-emergence of the crop.

An object of the invention is also the use of the HPPD gene as a marker gene in the course of the "transformation-regeneration" cycle of a plant species and selection on the above herbicide.

BRIEF DESCRIPTION OF THE DRAWINGS

FIG. 1 shows the protein sequence of HPPD of Pseudomonas sp. strain P.J. 874. and the theoretical nucleotide sequence of the coding part. Arrows show regions used for amplification.

FIG. 3 is a comparison of the amino acid sequence of HPPD of *P. fluorescens* A32 and HPPD of Pseudomonas sp. P.J. 874, showing both consensus sequence and differences between the sequences.

Figure 2:
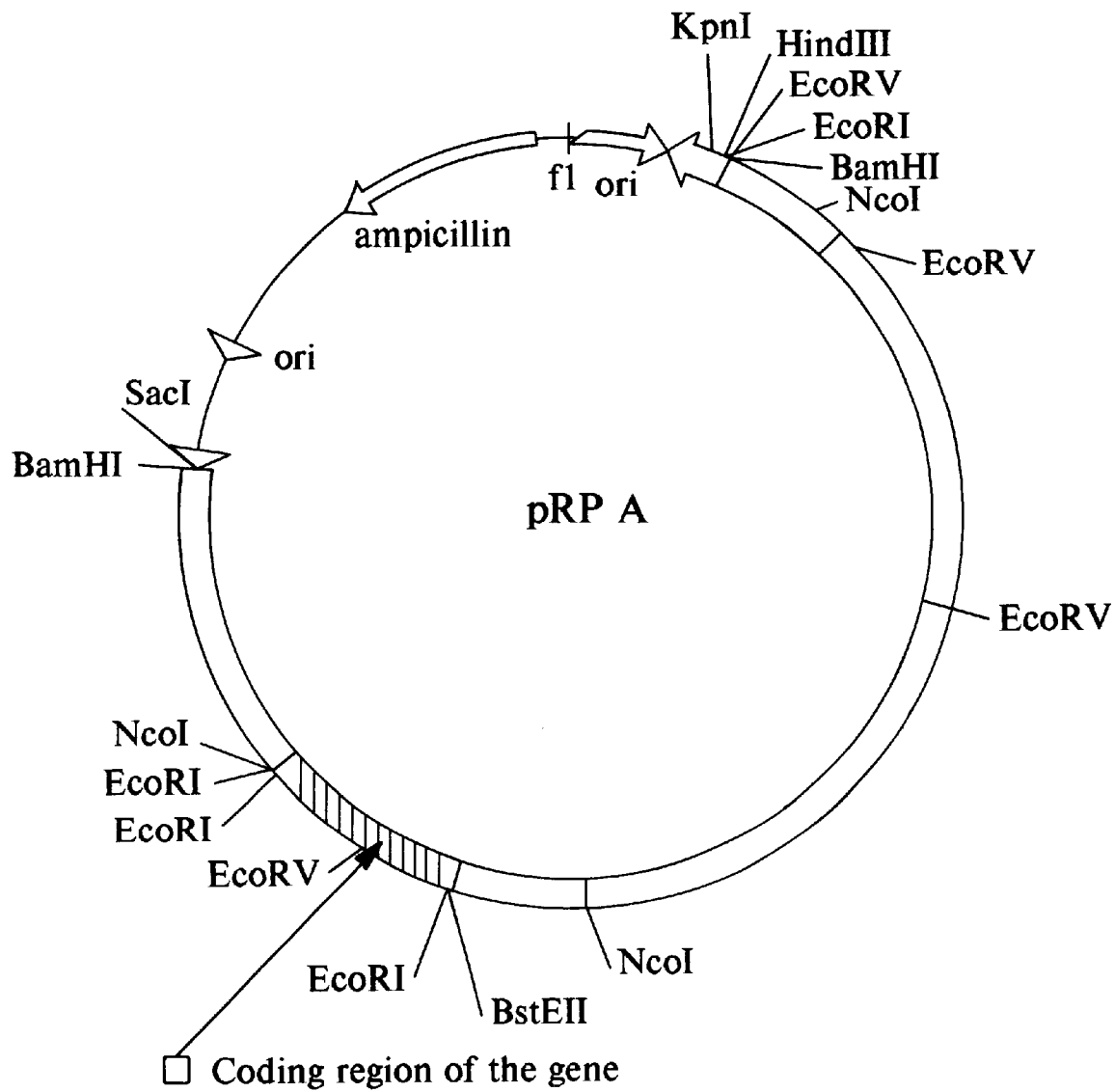
FIG. 2 shows a restriction map of the plasmid pRP A which contains the HPPD gene of *P. fluorescens* A32.

The different aspects of the invention will be better understood with the aid of the experimental examples below.

EXAMPLE 1

Isolation of the HPPD Gene of *P. fluorescens* A32

Starting from the amino-acid sequence of HPPD of Pseudomonas sp. P.J. 874 (published by Rüetschi U. et al., 1992, Eur. J. Biochem. 205: 459–466), the sequence of different oligonucleotides is deduced in order to amplify by PCR a part of the coding sequence of HPPD of *P. fluorescens* A 32 (isolated by McKellar, R. C. 1982, J. Appl. Bacteriol., 53: 305–316). An amplification fragment of the gene of this HPPD has been used to screen a partial genomic bank of *P. fluorescens* A32 and then to isolate the gene coding for this enzyme.

A) Preparation of genomic DNA of *P. fluorescens* A32

The bacteria was cultivated in 40 ml of M63 minimum medium (KH$_2$PO$_4$ 13.6 g/l, (NH$_4$)$_2$SO$_4$ 2 g/l, MgSO$_4$ 0.2 g/l, FeSO$_4$ 0.005 g/l, pH 7 plus L-tyrosine 10 mM as the sole carbon source) at 28° C. for 48 hours.

After washing, the cells are taken up in 1 ml of lysis buffer (100 mM tris HCl, pH 8.3, 1.4 M NaCl and 10 mM EDTA) and incubated for 10 minutes at 65° C. After a phenol/chloroform treatment (24:1) and a chloroform treatment, the nucleic acids are precipitated by addition of one volume of isopropanol, then taken up in 300 µl of sterile water and treated with final 10 µg/ml RNAse. The DNA is treated afresh with phenol/chloroform, chloroform and reprecipitated by addition of 1/10 of the volume of 3 M sodium acetate, pH 5 and 2 volumes of ethanol. The DNA is then taken up in sterile water and determined.

B) Choice of the oligonucleotides and syntheses

Starting from the amino-acid sequence of HPPD of Pseudomonas sp. P.J. 874, five oligonucleotides are chosen, two directed in the terminal NH$_2$ direction of the protein towards the COOH terminal of the protein and three directed in the opposite direction (see FIG. 1). The choice was dictated by the two following rules:

a stable 3' end of the oligonucleotide, that is to say at least two bases without ambiguity.

the smallest degeneracy possible.

The oligonucleotides chosen have the following sequences:

P1: 5'TA(C/T)GA(G/A)AA(C/T)CCIATGGG3'

P2: 5'GA(G/A)ACIGGICCIATGGA3'

P3: 5'AA(C/T)TGCATIA(G/A)(G/A)AA(C/T)TC(C/T)TC3'

P4: 5'AAIGCIAC(G/A)TG(C/T)TG(T/G/A)ATICC3'

P5: 5'GC(C/T)TT(A/G)AA(A/G)TTCC(C/T)TCIC3'

They were synthesized on a Cyclone plus DNA synthesizer of the make MILLIPORE.

With these five oligonucleotides, the amplification fragments which must be obtained theoretically by PCR starting from the sequence SEQ ID No. 1 have the following sizes:

with the primers P1 and P3 - - ->approximately 690 bp
with the primers P1 and P4 - - ->approximately 720 bp
with the primers P1 and P5 - - ->approximately 1000 bp
with the primers P2 and P3 - - ->approximately 390 bp
with the primers P2 and P4 - - ->approximately 420 bp
with the primers P2 and P5 - - ->approximately 700 bp C) Amplification of a coding part of HPPD of *P. fluorescens* A32

The amplifications were carried out on a PERKIN ELMER 9600 PCR apparatus and with PERKIN ELMER Taq polymerase with its buffer under standard conditions, that is to say for 50 µl of reaction mixture there are dNTP at 200 µM, primers at 20 µM, 2.5 units of Taq polymerase and 2.5 µg of DNA of *P. fluorescens* A32.

The amplification programme used is 5 min at 95° C. and then 35<45 sec 95° C., 45 sec 49° C., 1 min 72° C.>cycles followed by 5 min at 72° C.

Under these conditions, all the amplification fragments obtained have a size compatible with the theoretical sizes given above, which is a good indication of the specificity of the amplifications.

The amplification fragments obtained with the sets of primers P1/P4, P1/P5 and P2/P4 are ligated into pBSII SK(-) after digestion of this plasmid by Eco RV and treatment with the terminal transferase in the presence of ddTTP as described in HOLTON T. A. and GRAHAM M. W. 1991, N.A.R., Vol. 19, No. 5, p. 1156.

A clone of each of the three types is partially sequenced; this allows it to be confirmed that a part of the coding region of the HPPD of *P. fluorescens* A32 has been well amplified in the three cases. The P1/P4 fragment is retained as probe in order to screen a partial genomic bank of *P. fluorescens* A32 and to isolate the complete gene of the HPPD.

D) Isolation of the gene

By Southern it is shown that a 7 Kbp fragment hybridizes, after digestion of the DNA of *P. fluorescens* A32 by the restriction enzyme BamHI, with the probe HPPD P1/P4. 400 µg of DNA of *P. fluorescens* A32 are thus digested with the restriction enzyme BamHI and the DNA fragments making up approximately 7 Kbp are purified on agarose gel.

These fragments are ligated into pBSII SK(-), the latter is digested with BamHI and dephosphorylated by treatment with alkaline phosphatase. After transformation in *E. coli* DH10b, the partial genomic bank is screened with the probe HPPD P1/P4.

A positive clone was isolated and called pRP A. Its simplified map is given in FIG. 2. On this map is indicated the position of the coding part of the HPPD gene. It is composed of 1077 nucleotides which code for 358 amino acids (see SEQ ID No. 1). The HPPD of *P. fluorescens* A32 has a good amino-acid homology with that of Pseudomonas sp. strain P.J. 874, in fact there is 92% agreement between these two proteins (see FIG. 3).

EXAMPLE 2
Construction of Two Chimeric Genes

To confer plant tolerance to herbicides inhibiting HPPD, two chimeric genes are constructed:

The first consists in putting the coding part of the HPPD gene of *P. fluorescens* A32 under the control of the double histone promoter (European Patent No. 0 507 698) followed by tobacco etch virus translational enhancer (TEV) (pRTL-GUS (Carrington and Freed, 1990; J. Virol. 64: 1590–1597)) with the terminator of the nopaline synthase gene. The HPPD will then be localized in the cytoplasm.

The second will be identical to the first, except that the optimized transit peptide (OTP) is intercalated between the TEV transcription activator and the coding part of the HPPD (European Application EP No. 0 508 909). The HPPD will then be localized in the chloroplast.

A) Construction of the vector pRPA-RD-153:

pRDA-RD-11 A derivative of pBS-II SK(−) (Stratagene catalog #212206) containing the polyadenylation site of nopaline synthase (NOS polyA) (European Application EP No. 0 652 286) is cloned between the KpnI and SalI sites. The KpmI site is transformed into a NotI site by treatment with T4 DNA polymerase I in the presence of 150 μM of deoxynucleotide triphosphates and then ligation with an NotI linker (Stratagene catalog #1029). An NOS polyA cloning cassette is thus obtained.

pRPA-RD-127: A derivative of pRPA-BL-466 (European Application EP No. 0 337 899) cloned in pRPA-RD-11 creating an expression cassette of the oxy gene and containing the promoter of the small subunit of ribulose biscarboxylase:

"promoter (SSU)-oxy gene-NOS polyA"

To create this plasmid, pRPA-BL-488 was digested with XbaI and HindIII to isolate a fragment of 1.9 kbp comprising the SSU promoter and the oxy gene which was ligated into the plasmid pRPA-RD-11, digested with compatible enzymes.

pRPA-RD-132: This is a derivative of pRPA-BL-488 (European Application EP No. 0 507 698) cloned into pRPA-RD-127 with creation of an expression cassette of the oxy gene with the double histone promoter:

"double histone promoter-oxy gene-NOS polyA"

To produce this plasmid, pRPA-BL-466 is digested with HindIII, treated with Klenow and then redigested with NcoI. The purified fragment of 1.35 kbp containing the histone double promoter H3A748 is ligated with the plasmid pRPA-RD-127 which had been digested with XbaI, treated with Klenow and redigested with NcoI.

pRPA-RD-153: This is a derivative of pRPA-RD-132 containing the translation activator of the tobacco etch virus (TEV). pRTL-GUS (Carrington and Freed, 1990; J. Virol. 64: 1590–1597) is digested with NcoI and EcoRI and the 150 bp fragment is ligated into pRPA-RD-132 digested with the same enzymes. An expression cassette containing the promoter:

"double histone promoter-TEV-oxy gene-NOS polyA" is thus created.

B) Construction of the vector pRPA-RD-185:

pUC19/GECA: A derivative of pUC-19 (Gibco catalog #15364–011) containing numerous cloning sites. pUC-19 is digested with EcoRI and ligated with the oligonucleotide linker 1:

Linker 1: AATTGGGCCA GTCAGGCCGT TTAAAC-CCTA GGGGGCCCG

CCCGGT CAGTCCGGCA AATTTGGGAT CCCCCGGGC TTAA

The selected clone contains an EcoRI site followed by polylinker which contains the following sites: EcoRI, ApaI, AvrII, PmeI, SfiI, SacI, KpnI, SmaI, BamHI, XbaI, SalI, PstI, SphI and HindIII.

pRPA-RD-185: this is a derivative of pUC19/GECA containing a modified polylinker. pUC19/GECA is digested with HindIII and ligated with the oligonucleotide linker 2:

Linker 2: AGCTTTTAAT TAAGGCGCGC CCTC-GAGCCT GGTTCAGGG

AAATTA ATTCCGCGCG GGAGCTCGGA CCAAGTCCC TCGA

The selected clone contains a HindIII site in the centre of the polylinker which now contains the following sites: EcoRI, ApaI, AvrII, PmeI, SfiI, SacI, KpnI, SmaI, BamHI, XbaI, SalI, PstI, SphI, HindIII, PacI, AscI, XhoI and EcoNI.

C) Construction of the vector pRP T:

pRP O: a derivative of pRPA-RD-153 containing an expression cassette of HPPD, double histone promoter-TEV-HPPD gene-terminator Nos. To produce pRP O, pRPA-RD153 is digested with HindIII, treated with Klenow and then redigested with NcoI to remove the oxy gene and replace it by the HPPD gene coming from the pRP A plasmid by BstEII digestion, Klenow treatment and redigestion with NcoI.

pRP R: to obtain the plasmid, pRP O was digested with PvuII and SacI, the chimeric gene was purified and then ligated into pRPA-RD-185 and the latter was digested with PvuII and SacI.

pRP T: was obtained by ligation of the chimeric gene-coming from pRP R after digestion with SacI and HindIII in the plasmid pRPA-BL 150 alpha2 digested with the same enzymes (European Application EP No. 0 508 909).

The chimeric gene of the pRP T vector thus has the following structure:

| Double histone promoter | TEV | Coding region of HPPD | nos terminator |
| --- | --- | --- | --- |

D) Construction of the pRP V vector pRP P: this is a derivative of pRPA-RD-7 (European Application EP No. 0 652 286) containing the optimized transit peptide followed by the HPPD gene. It was obtained by ligation of the coding part of HPPD coming from pRP A by BetEII and NcoI digestion, Klenow treatment and from the plasmid pRPA-RD-7, the latter digested with SphI and AccI and treated with DNAse polymerase T4.

pRP Q: a derivative of pRPA-RD-153 containing an expression cassette of HPPD, double histone promoter-TEV-OTP-HPPD gene-Nos terminator. To construct it, the plasmid pRPA-RD-153 is digested with SalI, treated with Klenow and then redigested with NcoI to remove the oxy gene and replace it by the HPPD gene released from the pRP P plasmid by BstEII digestion, Klenow treatment and redigestion with NcoI.

pRP S: to obtain it, the plasmid pRP Q was digested with PvuII and SacI to release the chimeric gene, which was ligated into pRPA-RD-185, the latter digested with PvuII and SacI.

pRP V: it was obtained by ligation of the chimeric gene released from pRP S, after digestion with SacI and HindIII, into the plasmid pRPA-BL 150 alpha2 (European Application EP No. 0 508 909).

The chimeric gene of the pRP Q vector thus has the following structure:

| Double histone promoter | TEV | OTP | Coding region of HPPD | nos terminator |
|---|---|---|---|---|

EXAMPLE 3
Transformation of the Industrial Tobacco PBD6

In order to determine the efficacy of these two chimeric genes, these were transferred to industrial tobacco PBD6 according to the transformation and regeneration procedures already described in European Application EP No. 0 508 909.

1) Transformation

The vector is introduced into the non-oncogenic strain of Agrobacterium EHA 101 (Hood et al., 1987) which carries the cosmid pTVK 291 (Komari et al., 1986). The transformation technique is based on the procedure of Horsh R. et al. (1985), Science, 227, 1229–1231.

2) Regeneration

The regeneration of the tobacco PBD6 (origin SEITA France) from foliar explants is carried out on a Murashige and Skoog (MS) base medium comprising 30 g/l of sucrose as well as 200 µg/ml of kanamycin. The foliar explants are selected on plants in the greenhouse or in vitro and transformed according to the foliar discs technique (Science 1985, Vol. 227, p. 1229–1231) in three successive steps: the first comprises the induction of shoots on an MS medium to which is added 30 g/l of sucrose containing 0.05 mg/l of naphthylacetic acid (NAA) and 2 mg/l of benzylaminopurine (BAP) for 15 days. The shoots formed during this step are then developed by culture on an MS medium to which is added 30 g/l of sucrose, but not containing any hormone, for 10 days. Developed shoots are then selected and cultured on an MS rooting medium of half salts, vitamins and sugars content and not containing any hormone. At the end of approximately 15 days, the rooted shoots are placed in earth.

EXAMPLE 4
Measurement of the Tolerance of the Tobacco to 4-[4-$CF_3$-2-(methylsulphonyl)benzoyl]-5-cyclopropylisoxazole: Post-Emergence Treatment On leaving in-vitro culture, the transformed tobacco plantlets were acclimatized in a greenhouse (60% relative humidity; temperature: 20° C. during the night and 23° C. during the day) for five weeks and then treated with 4-[4-$CF_3$-2-(methylsulphonyl)benzoyl]-5-cyclopropylisoxazole.

The control tobacco, non-transformed and treated with 4-[4-$CF_3$-2-(methylsulphonyl)benzoyl]-5-cyclopropylisoxazole in doses ranging from 50 to 400 g/ha, develops chloroses in approximately 72 hours, which intensify to develop into very pronounced necroses in a week (covering approximately 80% of the terminal leaves).

After transformation, this same tobacco, which overexpresses the HPPD of *P. fluoreacens*, is very well protected against treatment with 4-[4-$CF_3$-2-(methylsulphonyl) benzoyl]-5-cyclopropylisoxazole at a dose of 400 g/ha.

If the overexpressed enzyme is in the cytoplasm, that is to say if the transformation was carried out with the gene carried by the vector pRP T, then the plant shows very slight chloroses which are all localized on the intermediate leaves.

If the overexpressed enzyme is in the chloroplast, that is to say if the transformation was carried out with the gene carried by the vector pRP V, then the plant is perfectly protected and does not show any symptoms.

EXAMPLE 5
Measurement of the Tolerance of the Tobacco to 4-[4-$CF_3$-2-(methylsulphonyl)benzoyl]-5-cyclopropylisoxazole: Pre-Emergence Treatment a) in vitro test Tobacco seeds harvested from plants from the "transformation-regeneration" cycle and resistant to isoxaflutole foliar treatment are used at a dose of 400 g/h described in Examples 1 to 3.

These seeds were sown in boxes containing plant agar at 10 g/l and isoxaflutole at different concentrations ranging from 0 to 1 mg/l. Germination was then carried out at 25° C. with a photoperiod of 12 hours of light/12 hours of darkness.

According to this protocol, wild tobacco seeds were germinated as well as seeds of the two types of transgenic tobacco, that is to say CY tobaccos, with localization of the HPPD in the cytoplasm, and the CO tobaccos with localization of the HPPD in chloroplast.

Resistance measurements are carried out visually between 2 and 3 weeks after sowing.

The results are recorded in the table below.

| isoxaflutole concentration | Wild tobacco | CY tobacco | CO tobacco |
|---|---|---|---|
| 0 mg/l | 100% of the seeds germinate without symptoms° | 100% of the seeds germinate without symptoms° | 100% of the seeds germinate without symptoms |
| 0.05 mg/l | 20% of the seeds germinate and show symptoms° | 75% of the seeds germinate* without symptoms° | 75% of the seeds germinate* without symptoms° |
| 0.1 mg/l | no germination | 75% of the seeds germinate* without symptoms° | 75% of the seeds germinate* without symptoms° |
| 0.5 mg/l | no germination | 75% of the seeds germinate* without symptoms° | 75% of the seeds germinate* without symptoms° |
| 1 mg/l | no germination | 75% of the seeds germinate* with slight symptoms° | 75% of the seeds germinate* without symptoms° |

°the symptoms which the plantlets show in the course of germination are more or less significant deformations of the cotyledons and above all a bleaching of the tissues which are normally photosynthetic and thus green.
*75% of the seeds germinate because seeds from the self-fertilization of single-locus plants coming from the "transformation-regeneration" cycle and thus only carrying the tolerance gene on a chromosome were sown. Working in the same way with the following products, Product No. 51 of American Patent 4 780 127, the same results are obtained at a concentration of 0 mg/l and 0.1 mg/l on wild tobacco and CO tobacco.

b) Greenhouse Test

Measurement is carried out as in Example 4, apart from the treatment being carried out pre-emergence, 24 hours before sowing. Wild sowing is carried out normally. Under these conditions, it is observed that, for the non-treated control sowings, there is no germination for any dose of herbicide at least equal to 10 g/ha. On the contrary, the CY tobaccos do not show any symptoms, such as defined in paragraph a), up to and including 100 g/ha. Similarly, the CO tobaccos do not show any symptoms, such as defined in paragraph a), up to and including 200 g/ha.

These results show clearly that the HPPD gene of *P. fluorescens* confers a tolerance to the tobacco against pre-emergence treatments with isoxaflutole. This tolerance is better if the protein is localized in the chloroplast in place of the cytoplasm.

EXAMPLE 6

With the aim of studying whether the HPPD gene of *Pseudomonas fluorescens* can be used as a marker gene in the course of the "transformation-regeneration" cycle of a plant species, tobacco was transformed with the HPPD gene and transformed plants were obtained after selection on isoxaflutole.

Material and Methods and Results

The chimeric gene pRP V described below is transferred into industrial tobacco PBD6 according to the transformation and regeneration procedures already described in European Application EP No. 0 508 909.

The chimeric gene of the vector pRP V has the following structure:

| Double histone promoter | TEV | OTP | Coding region of HPPD | nos terminator |

1) Transformation

The vector is introduced into the Agrobacterium EHA 101 non-oncogenic strain (Hood et al., 1987) which carries the cosmid pTVK 291 (Komari et al., 1986). The transformation technique is based on the procedure of Horsh et al. (1985).

2) Regeneration

The regeneration of the tobacco PBD6 (origin SEITA France) from foliar explants is carried out on a Murashige and Skoog (MS) base medium comprising 30 g/l of sucrose as well as 350 mg/l of cefotaxime and 1 mg/l of isoxaflutol. The foliar explants are selected on plants in a greenhouse or in vitro and transformed according to the foliar discs technique (Science 1985, Vol. 227, p. 1229–1231) in three successive steps: the first comprises the induction of shoots on an MS medium to which is added 30 g/l of sucrose containing 0.05 mg/l of naphthylacetic acid (NAA) and 2 mg/l of benzylaminopurine (BAP) for 15 days and 1 mg/l of isoxaflutole. The green shoots formed in the course of this step are then developed by culture on an MS medium to which is added 30 g/l of sucrose and 1 mg/l of isoxaflutole, but not containing hormone, for 10 days. Developed shoots are then selected and are cultured on an MS rooting medium of half salts, vitamins and sugars content and 1 mg/l of isoxaflutole and not containing any hormone. At the end of approximately 15 days, the rooted shoots are placed in earth.

All the plantlets obtained according to this protocol are analysed by PCR with specific primers of the HPPD of *P. fluorescens*. This PCR analysis has enabled it to be confirmed that all the plantlets thus obtained have well integrated the HPPD gene.

In conclusion, this assay confirms that the HPPD gene can be used as marker gene and that, associated with this gene, isoxaflutole can be a good selection agent.

EXAMPLES 7 AND 8

Isolation of the HPPD Gene of *Arabidopsis Thaliana* and of the HPPD Gene of Carrot (*Daucus Carotta*)

a) Construction of CDNA Banks mRNAs extracted from young plantlets of *Arabidopsis thaliana* and mRNAs extracted from carrot cells in culture served to construct two cDNA banks in the vector Uni Zap™ XR marketed by the company Stratagen, following the protocol recommended by this company.

b) Screening of the cDNA Banks These two banks were screened with the aid of a probe corresponding to a cDNA of *Arabidopsis thaliana* of partial length, obtained via the Arabidopsis Biological Resource Center (Ohio, USA) and indexed: EST clone No. 91B13T7. This clone is formed of approximately 500 base pairs of which only 228 have been sequenced by the MSU-DOE Plant Research Laboratory in the context of random sequencing of cDNA of *Arabidopsis thaliana*. We completely sequenced the 500 base pairs before using this clone to screen our cDNA banks of *Arabidopsis thaliana* and of carrot with the aid of the classical technique of hybridization of lysis plaques (reference ?).

c) A cDNA of *Arabidopsis thaliana* (SEQ ID No. 2) corresponding to 1338 base pairs was obtained. This cDNA has a translation initiation start codon in position 25 and a translation end codon in position 1336. This cDNA is thus complete and codes for a protein of 445 amino acids.

d) A cDNA of carrot (*Daucus carotta*) (SEQ ID No. 3) corresponding to 1329 base pairs was obtained. This cDNA has a translation initiation start codon in position 1 and a translation finish codon in position 1329. This cDNA is thus complete and codes for a protein of 442 amino acids.

The sequences illustrated are the following:

SEQ ID No. 1 Sequence of the HPPD gene of *Pseudomonas fluorescens* A32

SEQ ID No. 2 cDNA sequence of HPPD of *Arabidopsis thaliana*

SEQ ID No. 3 cDNA sequence of HPPD of *Daucus carotta*

FIG. 1 represents the protein sequence of the HPPD of Pseudomonas sp. strain P.J 874 and the theoretical nucleotide sequence of the corresponding coding part; the five oligonucleotides chosen to carry out the amplification of a part of.this coding region are symbolized by the five arrows.

FIG. 2 represents the mapping of the plasmid with the genomic DNA fragment of 7 kb comprising the gene of the HPPD of *P. fluorescens* A32.

FIG. 3 gives the comparison of the amino-acid sequences of the HPPD of *P fluorescens* A32 and of the HPPD of Pseudomonas sp. strain P.J.874 (only the divergant amino acids, between the two sequences are indicated) as well as the concensus sequence.

What is claimed is:

1. An isolated gene which expresses a hydroxyphenylpyruvate dioxygenase (HPPD) from Pseudomonas.

2. Sequence according to claim 1, characterized in that it is from *Pseudomonas fluorescens*.

3. A chimeric gene comprising, in the direction of transcription:
   at least one promoter regulation sequence from a gene expressing itself naturally in plants,
   a heterologous coding sequence under control of the promoter regulation sequence, and
   at least one polyadenylation sequence, characterized in that the coding sequence expresses hydroxyphenylpyruvate diogenase (HPPD).

4. Chimeric gene according to claim 3, characterized in that the promoter regulation sequence comprises at least one histone promoter.

5. Chimeric gene according to claim 3, characterized in that it comprises, between the promoter regulation sequence and the coding sequence, a transit peptide.

6. Chimeric gene according to claim 3, characterized in that it comprises, between the promoter regulation sequence and the coding sequence and, in the transcription direction, a sequence coding for a transit peptide of a plant gene coding for a plastid localization enzyme, a part sequence of the N-terminal mature part of a plant gene coding for a plastid localization enzyme, then a sequence coding for a second transit peptide of a plant gene coding for a plastid localization enzyme.

7. Chimeric gene according to claim 3, characterized in that it comprises, between the promoter regulation sequence and the coding sequence, a sequence of a transcription activator (enhancer).

8. A vector comprising a chimeric gene according to claim 3.

9. A plant which contains the chimeric gene as claimed in claim 3.

10. A method of selective herbicidal treatment of plants, which comprises applying an HPPD-inhibiting herbicide to the plant as claimed in claim 9.

11. The method of claim 10 wherein the herbicide is an isoxazole.

12. The method of claim 11, wherein the isoxazole is 4-[4-$CF_3$-2-methylsulfonylbenzoyl]-5-cyclopropyl isoxazole.

13. The method of claim 10 wherein the herbicide is a diketonitrile.

14. The method of claim 10 wherein the herbicide is a triketone.

15. The method of claim 10 wherein the herbicide is a sulcotrione.

* * * * *

UNITED STATES PATENT AND TRADEMARK OFFICE
CERTIFICATE OF CORRECTION

PATENT NO. : 6,268,549 B1  
DATED : July 31, 2001  
INVENTOR(S) : Sailland et al.

Page 1 of 1

It is certified that error appears in the above-identified patent and that said Letters Patent is hereby corrected as shown below:

Column 15, claim 3,  
Line 14, please delete "diogenase" and replace with -- dioxygenase --.

Column 15, claim 5,  
Line 20, Prior to "transit peptide", please insert -- sequence coding for a --.

Signed and Sealed this

Twelfth Day of March, 2002

Attest:

Attesting Officer

JAMES E. ROGAN  
Director of the United States Patent and Trademark Office